Figure 3A:
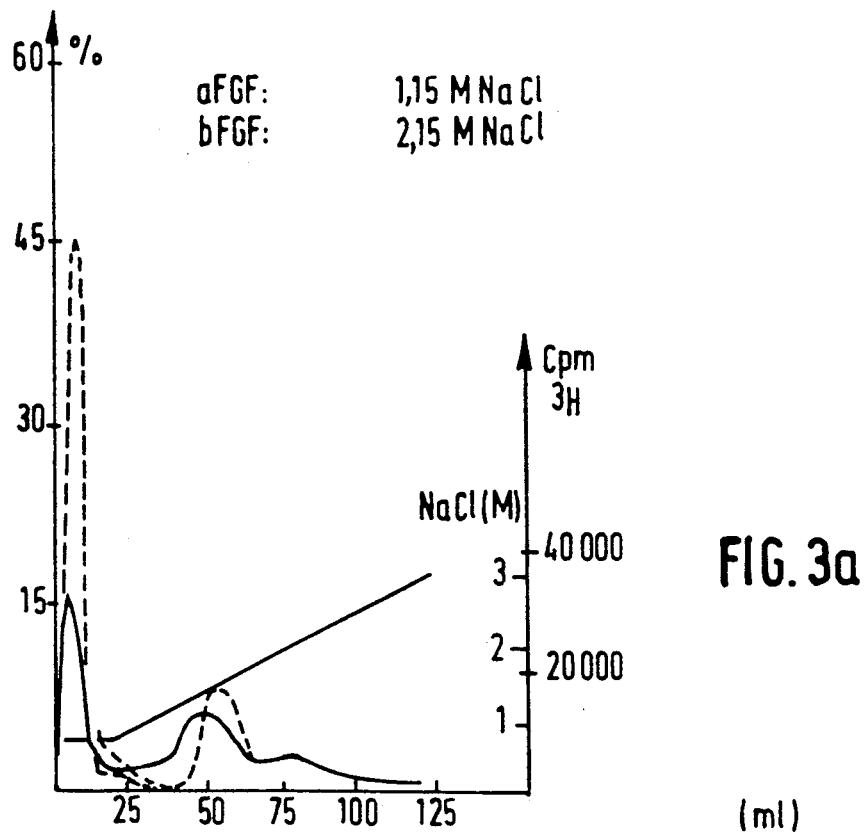

United States Patent [19]

Barritault et al.

[11] Patent Number: 5,122,597
[45] Date of Patent: Jun. 16, 1992

[54] APPLICATION OF RESINS CONSISTING OF FUNCTIONAL POLYMERS AS THE STATIONARY PHASE IN AFFINITY CHROMATOGRAPHY FOR THE PURIFICATION OF GROWTH FACTORS, AND CORRESPONDING PURIFICATION METHOD

[75] Inventors: Denis S. C. Barritault, Paris; Josette Badet née Genissel, Antony; José P. Courty, Villecresnes; Marie-Anne Dourges née Jacquot, Pierrelaye; Danielle Gulino née Debrac, Neuilly Plaisance; Jacqueline Jozefonvicz née Dorgebray, Lamorlaye, all of France

[73] Assignee: Centre National de la Recherche Scientifique (CNBS), Paris, France

[21] Appl. No.: 182,191

[22] Filed: Apr. 15, 1988

[30] Foreign Application Priority Data

Apr. 17, 1987 [FR] France .................................. 87 05546

[51] Int. Cl.⁵ .................................................. C07K 3/18
[52] U.S. Cl. ...................................... 530/399; 530/413; 530/412
[58] Field of Search ................. 530/413, 399, 412, 350

[56] References Cited

U.S. PATENT DOCUMENTS 4,755,379  7/1988  Jozefonvicz et al. .............. 424/83
4,785,079  11/1988  Gospodarowicz .................. 530/399

Primary Examiner—Robert A. Wax
Assistant Examiner—Keith C. Furman
Attorney, Agent, or Firm—Fleit, Jacobson, Cohn, Price, Holman & Stern

[57] ABSTRACT

The present invention relates to the application, as the stationary phase in affinity chromatography for the purification of the FGF type growth factors, of the polymers or copolymers onto which $-SO_3H$ and $-SO_3M$ groups are randomly bound, groups in which M denotes a physiologically acceptable metal, as well as, preferably, $-SO_2R$ groups, in which R denotes a radical obtained by removal of a hydrogen atom from the amino group of an amino acid or an amino acid derivative.

The invention relates also to the obtaining of a purified bFGF or aFGF growth factor, or a mixture of these growth factors, consisting in carrying out an affinity chromatography on a resin such as defined hereinabove, by carrying out an elution with a neutral pH buffer having an ionic strength equivalent to that of a 0.15 M to 2.5 M NaCl solution.

15 Claims, 3 Drawing Sheets

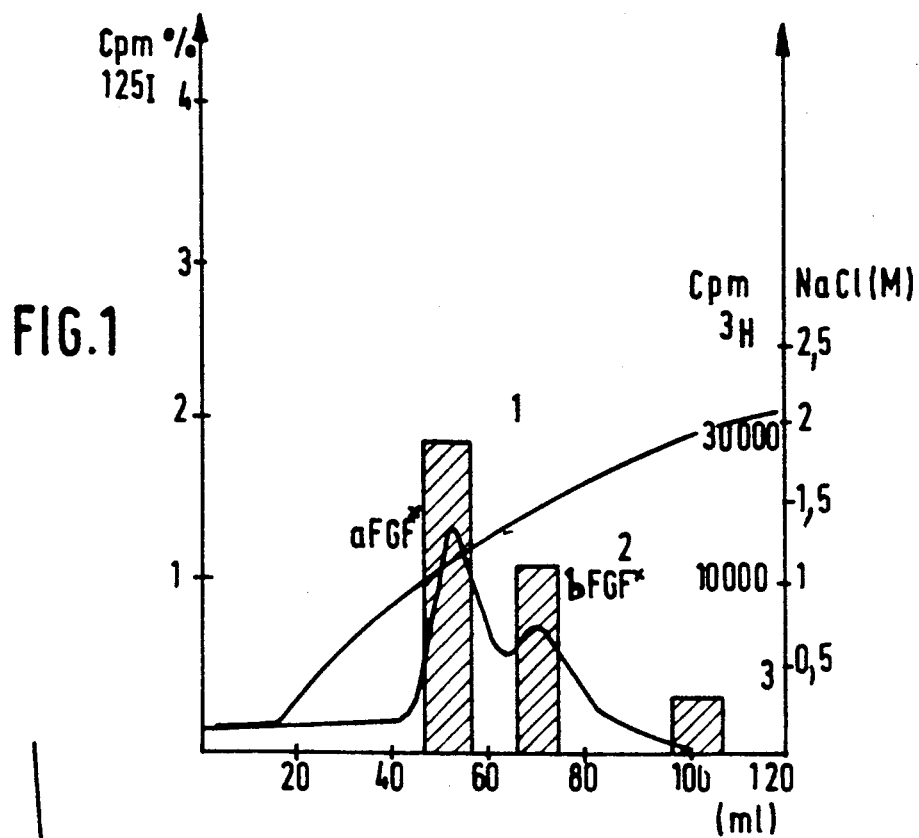
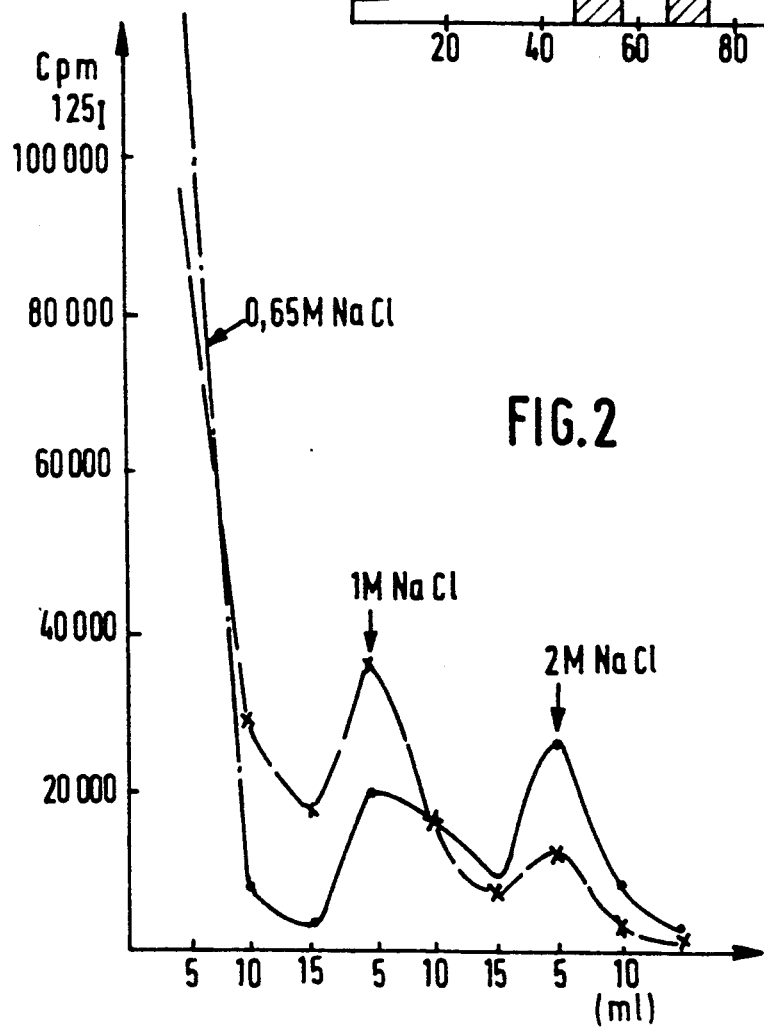

APPLICATION OF RESINS CONSISTING OF FUNCTIONAL POLYMERS AS THE STATIONARY PHASE IN AFFINITY CHROMATOGRAPHY FOR THE PURIFICATION OF GROWTH FACTORS, AND CORRESPONDING PURIFICATION METHOD

FIELD OF THE INVENTION

Background

The present invention relates to the purification of growth factors by affinity chromatography on resins carrying groups able to confer upon them a selective affinity for these growth factors.

In the literature, growth factor activities have been described which are defined as extracts containing compounds which are able to influence cellular migration and proliferation, especially by playing an important role in the neovascularization of healthy or pathological tissues. These growth factor activities are obtained from a large number of tissues, especially from the pituitary gland, the brain, the hypothalamus, the retina and various eye tissues, from cartilage and chondrosarcomas, and also from the kidney, the liver, the placenta, the corpus luteum, the muscle and the like. It emerges from numerous research papers that, among these factors, those which can be purified by affinity chromatography on Heparin Sepharose belong to two groups having these activities. These proteins have been separated and characterized and their primary structure has been elucidated.

The first group of these proteins has been described under the names FGF (or basic FGF), AGF2 (astroglial growth factor), BDGFI, β-HBGF (beta heparin binding growth factor), BDGF$_1$ (brain derived growth factor); as for the second, it has been described under the names ECGF, acidic FGF, AGF1, EDGFII, RDGF (retinal derived growth factor), α-HBGF, BDGF$_2$. For simplification, these known growth factors will be called bFGF and aFGF. The aFGF growth factors show an isoelectric point of between about 5 and 5.8 and a molecular weight of between 16,000 and 18,000 daltons. As for the bFGF growth factors, they show an isoelectric point of the order of 9 to 10 and a molecular weight of between 16,000 and 19,000 daltons. As a literature reference relating to these growth factors, there may be mentioned R. R. LOBB et al, "Analytical Biochemistry 154, 1-14 (1986)" as well as J. Courty et al, in "Biochem Biophys. Res. Commun., 136, 102-108 (1986)".

As was mentioned hereinabove, the FGF type growth factors are purified by affinity chromatography on polysaccharide-based resins on which heparin is bound. As an example of resins of this type, there may be mentioned the one which is marketed under the tradename "Heparin Sepharose" by the "PHARMACIA" company. On this resin, the aFGF factors are eluted with a neutral pH buffer having an ionic strength equivalent to that of an NaCl solution of close to 1M, and the bFGF factors are eluted with a neutral pH buffer having an ionic strength equivalent to that of an NaCl solution of between 1.5 and 2.0M. Thus, upon contacting of the "Heparin Sepharose" resin with the crude extract containing the growth factors, the elution of these is carried out with a sodium chloride gradient, for example.

The abovementioned chromatographic support, based on heparin, is a gel which allows only one use under low pressure, which considerably limits its use on an industrial scale. Moreover, heparin being a very heterogeneous polysaccharide (ie. a mixture of glycosaminoglycanes extracted from pig intestine and showing a wide molecular weight distribution), the chromatographic purifications using the "Heparin Sepharose" resin are not always reproducible and depend on the heparin batch which was coupled onto the starting resin.

In order to overcome these disadvantages, totally artificial supports were sought for this application, the biological properties of these being analogous to those of heparin, which possess good mechanical properties making it possible to purify these growth factors under high pressure, and which are able to withstand the chemical conditions imposed by their regeneration after use in chromatography.

SUMMARY OF THE INVENTION

A family of well-defined functional polymers has now been discovered which answers the problem stated and which can thus advantageously replace the "Heparin Sepharose" resin for the purification of FGF type growth factors by liquid chromatography.

These resins consist of polymers or copolymers onto which are randomly bound —SO$_3$H and —SO$_3$M groups (where M denotes a physiologically acceptable metal), as well as, preferably, also groups of formula —SO$_2$R (where R denotes a radical obtained by removal of a hydrogen atom from the amino group of an amino acid or of an amino acid derivative). These chemical groups are advantageously irreversibly bound by crosslinking.

The present invention thus relates first to the use of this resin family as the stationary phase in affinity chromatography for the purification of growth factors.

DETAILS

The polymeric or copolymeric starting support used is chosen especially from among polystyrene, polysaccharides, cellulose polyesters, cellulose polyethers, poly(vinyl acetate), poly(vinyl chloride), polyisoprene, polybutadiene, and the copolymers of styrene, cellulose esters, cellulose ethers, vinyl acetate, vinyl chloride, isoprene and butadiene.

Polystyrene may be mentioned as a particularly advantageous polymer.

Furthermore, the polymers or copolymers used are advantageously crosslinked products.

There is no special limitation as regards the amino acids, especially the α-amino acids and their derivatives, to be converted to the abovementioned radical R. For example, there may be mentioned in particular alanine, phenylalanine, aspartic and glutamic diacids, methionine, threonine, proline, hydroxyproline, serine and lysine.

Among the amino acids other than alpha-amino acids, there may be mentioned aminocaproic acid, aminovaleric acid and aminobutyric acid.

The resins which are used for the implementation of the invention are already known; they have been described particularly in French Patent No. 2,461,724.

The method for preparing them comprises a first step which consists in reacting chlorosulfonic acid with the chosen polymer, in a suitable solvent, in such a way as to obtain a chlorosulfonated polymer (i.e. carrying —SO$_2$Cl groups), and a second step consisting in either hydrolyzing said chlorosulfonated polymer with an MOH base in order to convert the —SO$_2$Cl groups into —SO$_3$M groups, or in reacting said chlorosulfonated polymer with the chosen amino acid, in the basic medium MOH, in order to convert the —SO$_2$Cl groups into —SO$_3$M groups and into —SO$_2$R groups.

The present invention relates also to a method for obtaining a purified aFGF or bFGF growth factor, or a mixture of these growth factors, characterized by the fact that it consists in carrying out an affinity chromatography on a resin, such as defined hereinabove. It is possible to carry out a chromatography under high pressure. Equally, the affinity chromatography can be carried out on several resins in series. Elution is carried out especially with a neutral pH buffer having an ionic strength equivalent to that of a 0.15M to 2.5M NaCl solution.

In order to illustrate further the subject of the present invention, several embodiments thereof will now be described by way of purely illustrative and nonlimiting examples.

In the first instance, the preparation of the various modified resins used will be described.

The starting polymer was a polystyrene consisting of a styrene and divinylbenzene copolymer (98/2 by weight), marketed by BIORAD. It was in the form of beads of a diameter of between about 40 and 80 μm. The commercial product was washed successively with a 1M NaOH solution, water, a 1M HCl solution, and water. It was dried under vacuum at 60° C.

The amino acids used were "FLUKA PURISS" reagents.

A) Preparation of PS-SO$_3$Na 25 g of polystyrene were left to swell overnight at room temperature in 200 ml of dichloromethane. A mixture of 160 ml of methylene chloride and 140 ml of chlorosulfonic acid was then added. The suspension was stirred for 4 hours at 40° C. The crude resin was then filtered, cautiously washed with methylene chloride and acetone. It was finally dried under vacuum at 50° C.

The chlorosulfonyl group level was determined in the following manner: 200 mg of chlorosulfonated polystyrene were hydrolyzed with 50 ml of a 1M NaOH solution for 24 hours under reflux. After acidification, the Cl$^-$ions were titrated with a 0.1M AgNO$_3$ solution while using a silver indicator electrode.

The sulfonated polystyrene was hydrolyzed quantitatively by 2M sodium hydroxide at room temperature. It was filtered, washed with water and dried under vacuum.

B) Preparation of PS-SO$_2$R

The chosen amino acid was used in an amount corresponding to two moles per chlorosulfonated group. The amino acid was dissolved in 125 ml of the 3:2 water-dioxan mixture, by adding a minimum amount of 4M sodium hydroxide. The pH was measured and 10 g of the chlorosulfonated polystyrene, such as obtained hereinabove (43 meq-SO$_2$Cl) were then added. The pH was then maintained at its initial value by adding 0.5M sodium hydroxide. The reaction was stopped when the pH remained stable. The polymer was then filtered, washed copiously with water, and then with 10$^{-2}$M sodium hydroxide and water. It was finally dried under vacuum.

The conditions for the synthesis of the resins used for the implementation of the invention examples are summarized in Table I following.

TABLE I

| Modified resin | Amino acid | Wt. of amino acid (g) | Reaction time (mn) | Initial 2M NaOH (ml) | 0.5M NaOH (ml) | Apparent pH |
|---|---|---|---|---|---|---|
| PSAla | Alanine | 7.5 | 47 | | 34 | 11 |
| PSPhe | Phenyl-alanine | 13.9 | 37 | 30 | 33.5 | 11.6 |
| PSGlu | Glutamic acid | 12.4 | 67 | 86 | 21 | 11.1 |
| PSAsp | Aspartic acid | 11.2 | 100 | 91.5 | 25.5 | 11.1 |
| PSMeth | Methionine | 12.5 | 16 | 53 | 20 | 11.2 |
| PSThreo | Threonine | 9.3 | 36 | 45 | 27 | 11.5 |
| PSSer | Serine | 8.4 | 58 | 46 | 32 | 11.6 |
| PSPro | Proline | 9.2 | 14 | 41 | 35.5 | 11.5 |

Weight of PS SO$_2$Cl=10 g, except in the case of the preparation of PSThreo where this is 9.3 g.

In some cases, especially if aspartic acid is used, it is preferable to bind the dimethyl ester of the corresponding acid onto the polyester, following up with a basic hydrolysis. The binding of the ester occurs in methylene dichloride medium in the presence of triethylamine (Et$_3$N). The working conditions are summarized in Table II.

TABLE II

| Resin modified by aspartic acid dimethyl ester | Reaction time (h) |
|---|---|
| PSAsp(OM)$_2$-a | 84 |
| PSAsp(OM)$_2$-b | 15 |
| PSAsp(OM)$_2$-c | 6 |
| Weight of PSSO$_2$Cl | 7 g |
| Weight of the asparatic acid dimethyl ester | 9 g |
| Volume of CH$_2$Cl$_2$ | 250 ml |
| Volume of Et$_3$N | 10.3 ml |
| Hydrolysis time | 24 h |
| Hydrolysis temperature | 40° C. |

The chemical compositions of these polymers are summarized in Table III following:

TABLE III

| Modified resins | Acidimetric titration (meq/g) | Microanalysis titration (meq/g) | % of amino acid units | % of SO$_3$ units |
|---|---|---|---|---|
| PSAla | 3.1 | 1.5 | 30.7 | 46.6 |
| PSPhe | 0.60 | 0.76 | 15.2 | 62.2 |
| PSGlu | 0.11 | 0.14 | 2.8 | 74.6 |
| PSAsp | 0.35 | 0.34 | 7 | 70.4 |
| PSMeth | 0.51 | 0.68 | 13.5 | 63.9 |
| PSThreo | 0.57 | 0.86 | 16 | 61.4 |
| PSSer | 0.94 | 0.76 | 14.3 | 65.7 |
| PSPro | 0.95 | 1.03 | 20.9 | 59.1 |

TABLE III-continued

| Modified resins | Acidimetric titration (meq/g) | Microanalysis titration (meq/g) | % of amino acid units | % of SO₃ units |
|---|---|---|---|---|
| PSAsp(OM)₂-a |  | 2.42 | 74.3 | 11.7 |
| PSAsp(OM)₂-b |  | 2.57 | 73.8 | 15.2 |
| PSAsp(OM)₂-c | 2.35 | 2.43 | 73 | 16 |
| PSHyPro |  |  | 24 | 56 |
| PSSO₃Na |  |  | 0 | 90 |

In the following there will be described, by way of illustration, the obtaining of the acid-soluble brain extract containing the aFGF and bFGF growth factors according to the technique described in French Patent Application No. 86/09476.

Each operation took place at 4° C. 4 kg of tissues were homogenized with a Turax mill in 1 liter of PBS buffer. The cellular fragments were removed by centrifugation at 10,000 g, for 45 mn (Beckman JA 10 Rotor). The supernatant, called crude extract, was adjusted to 20% (NH₄)₂SO₄ concentration and centrifuged for 45 minutes at 10,000 g. The second supernatant was passed over glass wool, in order to remove lipid traces, and then adjusted to 60% (NH₄)₂SO₄ concentration and centrifuged at 10,000 g for 45 minutes. The precipitate obtained was redissolved in a minimum volume of PBS (approximately 400 ml) and the pH of the solution was adjusted to 3.2 with glacial acetic acid, and then immediately centrifuged for 30 minutes at 10,000 g. The pH of the supernatant was readjusted to 7 with concentrated sodium hydroxide and was dialyzed extensively against PBS. The solution was then centrifuged for 30 minutes at 20,000 g (Beckman JA20 Rotor), in order to remove any trace of precipitate. This latter supernatant is called the acid-soluble extract.

Various affinity chromatographies were then performed on the resins according to the invention, such as those prepared hereinabove.

In order to make it easier to follow the purification, a small amount of purified and radioactive iodinelabeled aFGF (or bFGF) ($^{125}$I) (aFGF* or bFGF*) was added to the acid-soluble extract. The purification can thus be followed by measuring the radioactivity eluted in the fractions coming out of the column.

It was checked beforehand that the aFGF* and bFGF* factors show the same behavior as their native homologs in affinity chromatography. These experiments were carried out on the conventional "Heparin Sepharose" resin.

The first type of experiment consisted in following the radioactivity which was eluted from mixtures comprising acid-soluble extract and aFGF* or bFGF*.

The second type of experiment consisted in following the purification of the aFGF and bFGF from the acid-soluble extract by measuring the biological activity of the eluted fractions, in the absence of radioactive iodine-labeled factor. The biological tests used consisted in revealing the presence of the growth factor by examining the proliferation of target cells induced by the chromatographic fractions, by incorporating tritiated thymidine. As shown in FIG. 1, which gives the aFGF and bFGF chromatogram from the acid-soluble extract using a 150 ml NaCl gradient, the fractions which are rich in radioactivity contain the biological activity. The result is that the aFGF* and bFGF* factors represent good tracers of both biological activities (in FIG. 1  denotes the biological activity of the examined fractions ($^3$H cpm)).

The chromatographic tests which were carried out will now be described.

1 g of resin according to the invention was left to swell for 15 mn in 10 ml of PBS buffer and poured into an IBF 11 column (10 ml), at 0.5 ml/mn. 1 ml of the acid-soluble brain extract containing 4 mg of proteins, i.e. 4 mg per g of resin, was deposited on the column. The proteins retained were successively eluted with PBS solutions.

I—Tests carried out by using ionic strength stages:

These chromatographic tests were performed on PSAsp and PSSer resins. They were carried out by eluting with successive stages of 0.65M, 1M, 2M NaCl ionic strength.

These tests reveal a retention, and then a partial elution of the bFGF, when these two resins are used as the chromatographic gel. This is what emerges from FIG. 2 and from Table IV following:

TABLE IV

| Resins | % nonretained bFGF | % eluted bFGF* | % of definitively adsorbed bFGF* |
|---|---|---|---|
| PSAsp | 27 | 13 | 59 |
| PSSer | 30 | 20 | 50 |

FIG. 2 illustrates the elution of a bFGF*+acid-soluble extract mixture on PSSer (—o—) or on PSAsp (—x—x—).

The titration of the total protein concentrations (Bradford method), together with the determination of the radioactivity in the eluted fractions, makes it possible to assess an enrichment in growth factor. This enrichment is of between 10 and 20 for the fractions eluted with 1M or 2M NaCl.

II—Tests using a linear gradient

In this series of tests, the results of which are collated in Table V following, only the affinity with the bFGF factor was examined.

TABLE V

| Resins | % bFGF non adsorbed | % bFGF reversibly adsorbed | % bFGF irreversibly adsorbed | NaCl molarity bFGF elution (M) | % Proteins, Resins non adsorbed | % Proteins, Resins reversibly adsorbed | % Proteins, Resins irreversibly adsorbed | Enrichment |
|---|---|---|---|---|---|---|---|---|
| Heparin Sepharose | 30 | 30 | 29 | 1.5 | 62.5 | 1.5 | 36 | 20 |
| PSThreo | 80 | 10 | 1 | 1.2 | 90.6 | 0.4 | 9 | 40 |
| PSGlu (I) | 24 | 23 | 43 | 1.2 | 75.3 | 4.7 | 25 | 5 |
| PSGlu (II) | 36 | 19 | 41 | 1.1 | 79 | 0.3 | 21 | 63 |
| PSAsp | 37 | 13 | 43 |  | 80.9 | 0.9 | 18 | 14 |
| PSAsp (OM)₂ | 63 | 5 | 29 | 0.9 | 89.2 | 1.1 | 11 | 4.5 |
| PSPhe | 29 | 17 | 53 | 1.3 | 89.1 | 1.6 | 9 | 11 |

TABLE V-continued

| Resins | % bFGF | | | NaCl molarity bFGF elution (M) | % Proteins, Resins | | | Enrichment |
|---|---|---|---|---|---|---|---|---|
| | non adsorbed | reversibly adsorbed | irreversibly adsorbed | | non adsorbed | reversibly adsorbed | irreversibly adsorbed | |
| PSSO₃ | 20 | 14 | 62 | 1.7 | 69.8 | 1.8 | 28 | 8 |

Weight of resin per column = 1 g
I, II: successive chromatographic tests on the same column.

From this Table V, it is observed that the adsorption capacities are different, compared with those of Heparin Sepharose, tested by way of comparison.

In fact, 30% of the bFGF factor is reversibly adsorbed on the Heparin Sepharose resin, while 10% and 19% respectively are adsorbed on the PSThreo and PSGlu (II) resins under identical conditions. The irreversible adsorption of the bFGF factor is quite considerable, whatever the resin tested (29% for the "Heparin Sepharose" resin), except for the PSThreo resin. The nonspecific irreversible adsorption of the total proteins is markedly more pronounced in the case of the Heparin Sepharose resin.

A progressive saturation of the active sites was observed, after repeated use of the Heparin Sepharose columns, together with a very substantial diminution in the affinity of these resins for the growth factors. However, a purification on the same column of resins according to the invention promotes a better enrichment of the bFGF, and this was observed in the case of the PSGlu resin (Table V).

It can also be observed from this table that the intensity of the interactions involved between the bFGF factor and the various resins remains fairly constant, whatever the resin tested. In fact, the ionic strength required for the elution of the bFGF factor is of between 0.9 and 1.7M NaCl.

Figure 3B:
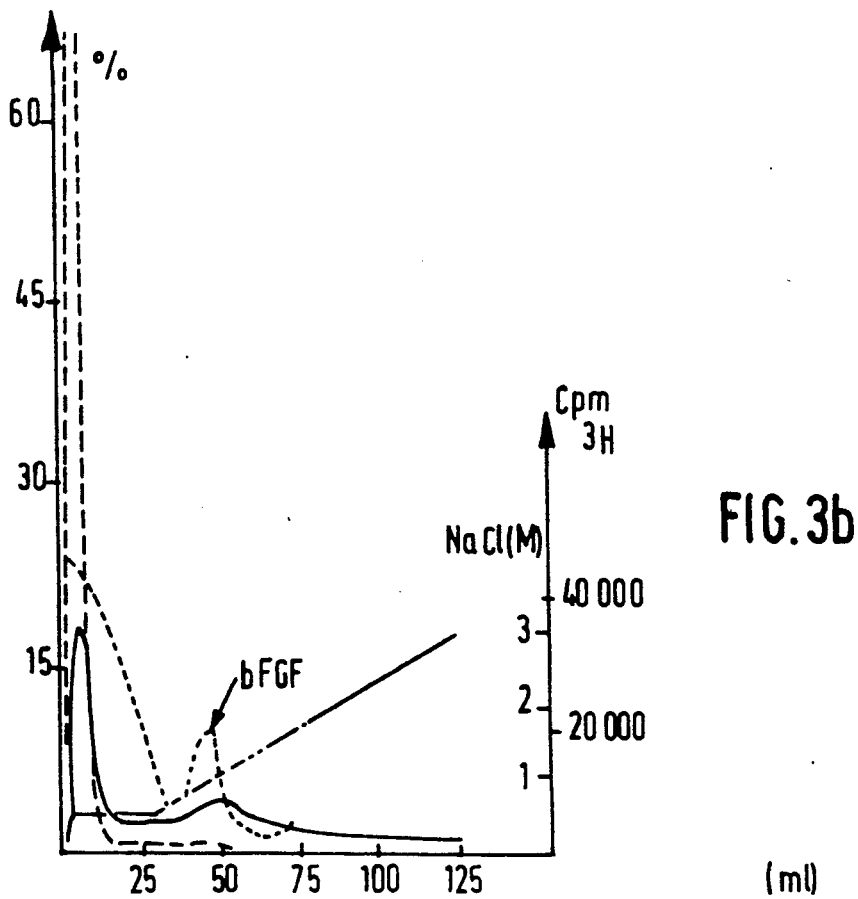
Figure 3C:
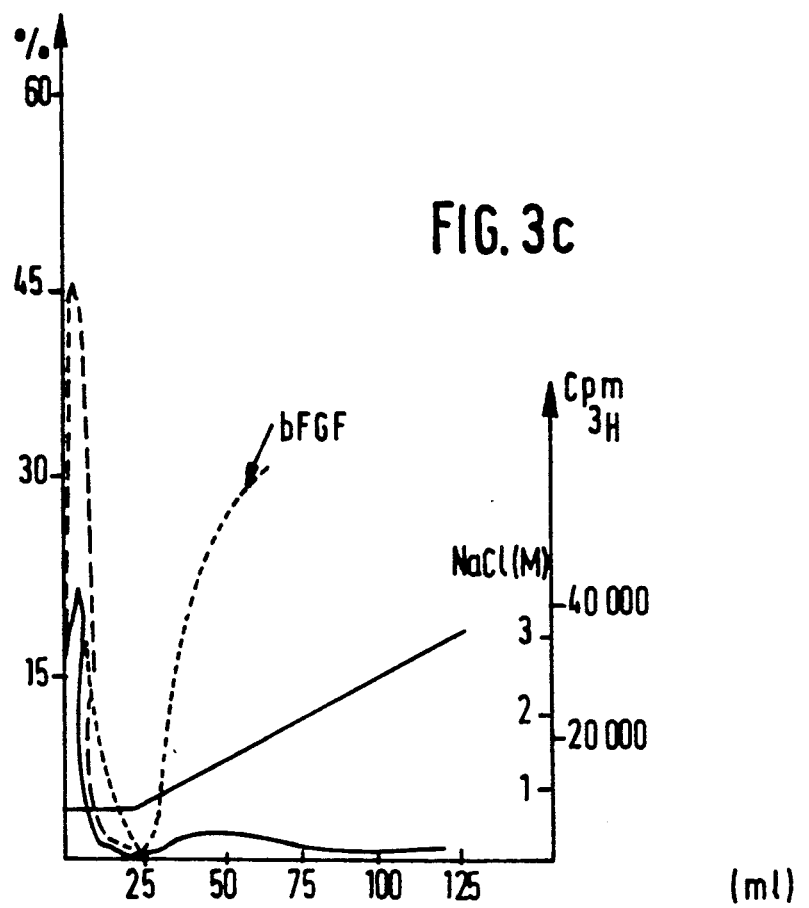

Moreover, in conjunction with the examination of the eluted radioactivity, biological activity tests (by incorporation of tritiated thymidine) were carried out for the Heparin Sepharose, PSGlu I and PSPhe resins. The results are shown in FIG. 3. Key to FIG. 3:

Chromatography on Heparin Sepharose and on resins of the invention of an acid-soluble extract/bFGF* mixture by using an NaCl elution gradient.
a) Heparin Sepharose; b) PSGlu; c) PSPhe
—: bFGF* ($^{125}$I cpm)
—: proteic concentration
—: biological activity ($^3$H cpm)
bFGF=2.15M NaCl elution
aFGF=1.15M NaCl elution The % of $^{125}$I detected radioactivity as well as the % of detected proteins were plotted as ordinates. The three types of curves were normed.

On these resins, although part of the biological activity is eluted with the fraction of nonadsorbed proteins, part of the biological activity is however desorbed with the NaCl gradient, and it is eluted at approximately the same volume as the radioactivity corresponding to the bFGF* factor. The NaCl molarity required for the desorption of the biological activity is of 1.6M for the Heparin Sepharose, of 1.2M for the two other resins according to the invention. In the case of the PSPhe resin, the biological activity recovered during the gradient is markedly greater than that recovered under the same conditions from Heparin Sepharose.

III—Tests using an automatic device.

Figure 4:
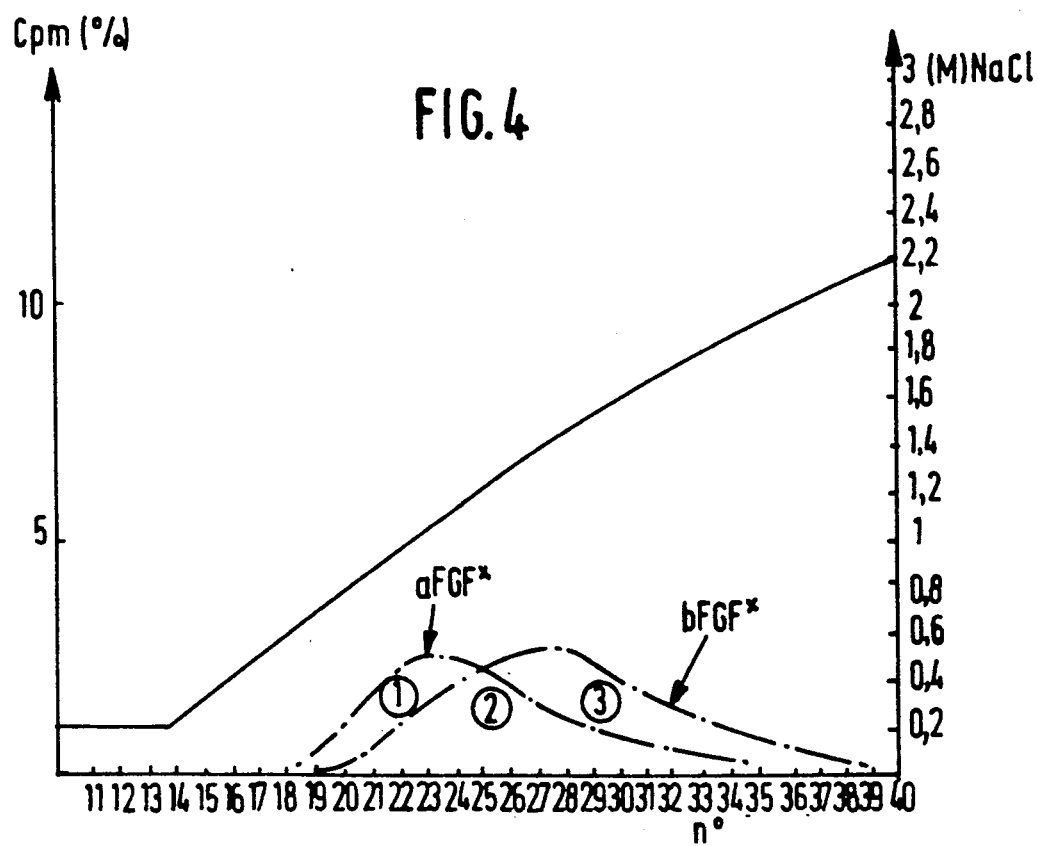

An automated chromatography system was perfected, allowing a good reproducibility of the NaCl gradient. The affinity of the bFGF factor and of the aFGF factor for the resins mentioned in Table VI was tested under these conditions. FIG. 4 shows that, in the case of the PSPhe resin, the bFGF and aFGF factors are slightly separated. Key to FIG. 4:

Chromatography on PSPhe of mixtures consisting of acid-soluble extract and either bFGF* or aFGF*, by using an NaCl elution gradient.
—bFGF* and aFGF*

Analysis of fractions 1, 2 and 3 by electrophoresis on polyacrylamide gel (SDS PAGE-silver coloration) reveals that fraction 3 contains only the two factors bFGF and aFGF.

TABLE VI

| | bFGF | | | aFGF | | |
|---|---|---|---|---|---|---|
| Resins | Retained and eluted % | NaCl* M | Efficiency** | Retained and eluted % | NaCl* M | Efficiency** |
| Heparin Sepharose | 49 | 1.5 | 1 | 28 | 1.1 | 1 |
| PSThreo | 11 | 1.4 | 0.55 | 2.2 | 0.5 | 0.07 |
| PSAla | 7 | 1.2 | 0.36 | 3.3 | 1 | 0.12 |
| PSMeth | 15 | 1.35 | 0.79 | 8.2 | 1 | 0.29 |
| PSPhe | 13 | 1.5 | 0.68 | 15 | 1.1 | 0.54 |
| PSPro | 10 | 0.9 | 0.53 | 1 | 0.8 | 0.04 |
| PSHyPro | 8 | 0.7 | 0.16 | 4 | 1.0 | 0.12 |
| PSSO₃Na | 14 | 1.5-2.0 | 0.29 | 14 | 1.15 | 0.48 |

*Maximum NaCl concentration of the eluent required for eluting the growth factor after preadsorption on the resin $$**\text{Efficiency} = \frac{\% \text{ retained and eluted on the resin}}{\% \text{ retained and eluted on Heparin Sepharose}}$$

IV—Tests using two columns in series

The results obtained on the PSThreo, PSAla and PSMeth as well as PSPhe resins, compared with those obtained under the same conditions on a Heparin Sepharose resin, are shown in the abovementioned Table VI.

These results were obtained starting from one and the same batch of growth factor acid-soluble extract, to which the bFGF* and aFGF* factors were successively added in order to facilitate analysis. These results reveal two groups of resins, a first group which retains only the bFGF factors (PSThreo and PSAla) and a second group which retains both growth factors bFGF and aFGF (PSPhe and PSMeth).

It is therefore possible to carry out a separation of the two purified factors by injecting the acid-soluble extract, as well as the bFGF* and aFGF* factors on a column packed with PSPhe, and then on a column packed with PSThreo. This double operation permits the two factors on the first column to be retained at an ionic strength of less than 0.7M NaCl and to subsequently carry out their successive elution on the second column.

It will be possible to carry out the elution on the second column PSThreo in an NaCl gradient, from 0.7M NaCl up to 1.4M NaCl. Under these conditions, the aFGF not retained on PSThreo, will be eluted before the bFGF which it is possible to recover in a 1.4M NaCl solution.

V—Tests obtained on high performance liquid chromatography

A stainless steel column, specially designed to operate under high pressure (of the order of 10 to 20 bars), is packed by percolation with approximately 1 g of the PSPhe resin. The column is connected to an apparatus comprising a high-pressure pump, an injector, one or two sensors and a microcomputer and integrator system making it possible to obtain the chromatograms of the injected species. The operation is carried out over a maximum of 30 minutes, in contrast to the low-pressure system which requires more than 10 hours. Furthermore, an automatic injection system makes it possible to carry out a preparative separation by proceeding with a series of injections of the acid-soluble extract, and then one single elution in a saline concentration gradient.

We claim:

1. In a method for conducting affinity chromatography, with a stationary phase, for purifying an FGF type growth factor, the improvement wherein the stationary phase comprises a polymer or copolymer resin support onto which chemical groups, selected from those consisting of —SO$_3$H groups and —SO$_3$M groups, are randomly bound and wherein M is a physiologically-acceptable metal.

2. A method of claim 1 wherein the polymer or copolymer resin is one onto which the chemical groups, —SO$_2$R groups, are also randomly bound, and R is a radical obtained by removal of a hydrogen atom from an amino group of an amino acid or of an amino acid ester.

3. A method of claim 2 wherein the amino acid is an α-amino acid and the amino acid ester is an α-amino acid ester.

4. A method of claim 2 wherein the amino acid is an α-amino acid selected from the group consisting of alanine, phenylalanine, aspartic acid, glutamic acid, methionine, threonine, proline, hydroxyproline, serine and lysine, and the amino acid ester is an ester of one of said amino acids.

5. A method of claim 1 wherein the chemical groups are irreversibly bound by crosslinking.

6. A method of one of claims 1, 13 and 16 wherein the resin support is a member selected from the group consisting of polystyrene, a polysaccharide, a cellulose polyester, a cellulose polyether, polyvinyl acetate, polyvinyl chloride, polyisoprene and polybutadiene or a copolymer of a member selected from the group consisting of styrene, a cellulose ester, a cellulose ether, vinyl acetate, vinyl chloride, isoprene and butadiene.

7. A method of claim 6 wherein the resin support is polystyrene.

8. A method of claim 1 wherein the FGF type growth factor is an aFGF growth factor, a bFGF growth factor or a mixture of these growth factors.

9. A method of claim 8 wherein the chromatography is a high-pressure chromatography.

10. A method of claim 8 wherein the affinity chromatography is carried out on several resins in series.

11. A method of one of claims 8 to 21 which comprises eluting the stationary phase with a neutral pH buffer having an ionic strength equivalent to that of a 0.15M to 2.5M NaCl solution.

12. A one-step method for purifying an FGF type growth factor which comprises conducting affinity chromatography with a stationary phase which comprises a polymer or copolymer resin onto which —SO$_3$H or —SO$_3$M groups are randomly bound and wherein M is a physiologically-acceptable metal.

13. A method of claim 12 wherein results are reproducible and the resin support is reusable.

14. A method of claim 12 wherein the resin support is a crosslinked resin.

15. A method of claim 1 wherein the polymer or copolymer resin support is one which is suitable for high-pressure chromatography.

* * * * *